United States Patent
Brooke et al.

(10) Patent No.: US 8,209,013 B2
(45) Date of Patent: Jun. 26, 2012

(54) THERAPEUTIC ELECTRICAL STIMULATION THAT AVOIDS UNDESIRABLE ACTIVATION

(75) Inventors: M. Jason Brooke, Minneapolis, MN (US); Alok S. Sathaye, Minneapolis, MN (US); Yanting Dong, Shoreview, MN (US); Scott Walczak, Eden Prairie, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 925 days.

(21) Appl. No.: 11/520,879

(22) Filed: Sep. 14, 2006

(65) Prior Publication Data

US 2008/0071318 A1    Mar. 20, 2008

(51) Int. Cl.
*A61N 1/362* (2006.01)
(52) U.S. Cl. ............ 607/28; 607/2; 607/9; 607/27
(58) Field of Classification Search ............ 607/2, 9, 607/27–28
See application file for complete search history.

(56) References Cited

U.S. PATENT DOCUMENTS

| | | | |
|---|---|---|---|
| 3,920,005 A | 11/1975 | Gombrich et al. | |
| 4,023,564 A | 5/1977 | Valiquette et al. | |
| 4,340,063 A * | 7/1982 | Maurer | 607/46 |
| 4,364,396 A | 12/1982 | Barthel | |
| 4,365,636 A | 12/1982 | Barker | |
| 4,458,692 A | 7/1984 | Simson | |
| 4,476,869 A | 10/1984 | Bihn | |
| 4,550,221 A | 10/1985 | Mabusth | |
| 4,552,154 A | 11/1985 | Hartlaub | |
| 4,562,841 A | 1/1986 | Brockway et al. | |
| 4,573,481 A | 3/1986 | Bullara | |
| 4,648,407 A | 3/1987 | Sackner | |
| 4,680,708 A | 7/1987 | Ambos et al. | |
| 4,686,332 A | 8/1987 | Greanias et al. | |
| 4,827,935 A | 5/1989 | Geddes et al. | |
| 4,860,766 A | 8/1989 | Sackner | |
| 4,878,497 A | 11/1989 | Callaghan et al. | |
| 4,928,688 A | 5/1990 | Mower | |
| 4,953,551 A | 9/1990 | Mehra et al. | |
| 4,979,507 A * | 12/1990 | Heinz et al. | 607/28 |
| 5,000,189 A | 3/1991 | Throne et al. | |
| 5,033,467 A | 7/1991 | Bocchi et al. | |
| 5,036,849 A | 8/1991 | Hauck et al. | |

(Continued)

FOREIGN PATENT DOCUMENTS

EP    0468720    1/1992

(Continued)

OTHER PUBLICATIONS

U.S. Appl. No. 10/955,393, filed Sep. 30, 2004, Freeberg.

(Continued)

*Primary Examiner* — Carl L Layno
*Assistant Examiner* — Jennifer Ghand
(74) *Attorney, Agent, or Firm* — Seager, Tufte & Wickhem LLC

(57) ABSTRACT

Energy parameters for electrical stimulation pulses that produce a desired activation, and avoid an undesirable activation, are determined. A strength-duration relationship for at least one desired activation produced by therapeutic electrical stimulation is measured. A strength-duration relationship for at least one undesirable activation produced by the therapeutic electrical stimulation is provided. A medical device selects, based on the desired and undesirable strength-duration relationships, one or more energy parameters for the therapeutic electrical stimulation that produce the desired activation and avoid the undesirable activation.

10 Claims, 7 Drawing Sheets

U.S. PATENT DOCUMENTS

| | | |
|---|---|---|
| 5,101,831 A | 4/1992 | Koyama et al. |
| 5,105,354 A | 4/1992 | Nishimura |
| 5,133,353 A | 7/1992 | Hauser |
| 5,146,918 A | 9/1992 | Kallok et al. |
| 5,170,784 A | 12/1992 | Ramon et al. |
| 5,178,156 A | 1/1993 | Takishima et al. |
| 5,179,945 A | 1/1993 | Van Hofwegen et al. |
| 5,184,615 A | 2/1993 | Nappholz et al. |
| 5,187,657 A | 2/1993 | Forbes |
| 5,203,348 A | 4/1993 | Dahl et al. |
| 5,209,229 A | 5/1993 | Gilli |
| 5,217,021 A | 6/1993 | Steinhaus et al. |
| 5,222,493 A | 6/1993 | Sholder |
| 5,230,337 A | 7/1993 | Dahl et al. |
| 5,233,983 A | 8/1993 | Markowitz |
| 5,261,400 A | 11/1993 | Bardy |
| 5,271,411 A | 12/1993 | Ripley et al. |
| 5,273,035 A | 12/1993 | Markowitz et al. |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,324,310 A | 6/1994 | Greeninger et al. |
| 5,331,966 A | 7/1994 | Bennett et al. |
| 5,331,996 A | 7/1994 | Ziehm |
| 5,333,095 A | 7/1994 | Stevenson et al. |
| 5,334,221 A | 8/1994 | Salo et al. |
| 5,335,657 A | 8/1994 | Terry, Jr. et al. |
| 5,350,410 A | 9/1994 | Kleks et al. |
| 5,353,788 A | 10/1994 | Miles |
| 5,360,442 A | 11/1994 | Dahl et al. |
| 5,366,496 A | 11/1994 | Dahl et al. |
| 5,372,606 A | 12/1994 | Lang et al. |
| 5,374,280 A | 12/1994 | den Dulk |
| 5,376,106 A | 12/1994 | Stahmann et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,529 A | 5/1995 | Hudrlik |
| 5,411,533 A | 5/1995 | Dubreuil |
| 5,411,539 A | 5/1995 | Neisz |
| 5,431,693 A | 7/1995 | Schroeppel |
| 5,439,482 A | 8/1995 | Adams et al. |
| 5,441,518 A | 8/1995 | Adams et al. |
| 5,443,485 A | 8/1995 | Housworth et al. |
| 5,447,519 A | 9/1995 | Peterson |
| 5,468,254 A | 11/1995 | Hahn et al. |
| 5,485,851 A | 1/1996 | Erickson |
| 5,517,983 A | 5/1996 | Deighan et al. |
| 5,520,191 A | 5/1996 | Karlsson et al. |
| 5,522,860 A | 6/1996 | Molin et al. |
| 5,531,779 A | 7/1996 | Dahl et al. |
| 5,534,017 A | 7/1996 | Van Krieken et al. |
| 5,540,727 A | 7/1996 | Tockman et al. |
| 5,540,732 A | 7/1996 | Testerman |
| 5,545,186 A | 8/1996 | Olson et al. |
| 5,545,202 A | 8/1996 | Dahl et al. |
| 5,549,655 A | 8/1996 | Erickson |
| 5,591,216 A | 1/1997 | Testerman et al. |
| 5,603,732 A | 2/1997 | Dahl et al. |
| 5,620,466 A | 4/1997 | Haefner et al. |
| 5,626,620 A | 5/1997 | Kieval et al. |
| 5,634,938 A | 6/1997 | Swanson et al. |
| 5,641,326 A | 6/1997 | Adams |
| 5,650,759 A | 7/1997 | Hittman et al. |
| 5,658,318 A | 8/1997 | Stroetmann et al. |
| 5,662,688 A | 9/1997 | Haefner et al. |
| 5,662,696 A | 9/1997 | Kroll et al. |
| 5,674,254 A | 10/1997 | van Krieken |
| 5,683,431 A | 11/1997 | Wang |
| 5,683,434 A | 11/1997 | Archer |
| 5,697,953 A | 12/1997 | Kroll et al. |
| 5,697,956 A | 12/1997 | Bornzin |
| 5,704,365 A | 1/1998 | Albrecht et al. |
| 5,713,933 A | 2/1998 | Condie et al. |
| 5,715,812 A | 2/1998 | Deighan et al. |
| 5,718,720 A | 2/1998 | Prutchi et al. |
| 5,724,984 A | 3/1998 | Arnold et al. |
| 5,735,883 A | 4/1998 | Paul et al. |
| 5,738,102 A | 4/1998 | Lemelson |
| 5,779,645 A | 7/1998 | Olson et al. |
| 5,814,087 A | 9/1998 | Renirie |
| 5,817,027 A | 10/1998 | Arand et al. |
| 5,827,326 A | 10/1998 | Kroll et al. |
| 5,836,987 A | 11/1998 | Baumann et al. |
| 5,844,506 A | 12/1998 | Binstead |
| 5,855,593 A | 1/1999 | Olson et al. |
| 5,857,977 A | 1/1999 | Caswell et al. |
| 5,860,918 A | 1/1999 | Schradi et al. |
| 5,861,011 A | 1/1999 | Stoop |
| 5,861,013 A | 1/1999 | Peck et al. |
| 5,871,512 A | 2/1999 | Hemming et al. |
| 5,873,898 A | 2/1999 | Hemming et al. |
| 5,876,353 A | 3/1999 | Riff |
| 5,895,414 A | 4/1999 | Sanchez-Zambrano |
| 5,916,243 A | 6/1999 | KenKnight et al. |
| 5,944,680 A | 8/1999 | Christopherson et al. |
| 5,957,956 A | 9/1999 | Kroll et al. |
| 5,964,778 A | 10/1999 | Fugoso et al. |
| 5,974,340 A | 10/1999 | Kadhiresan |
| 5,987,352 A | 11/1999 | Klein et al. |
| 6,026,320 A | 2/2000 | Carlson et al. |
| 6,038,474 A | 3/2000 | Zhu et al. |
| 6,044,298 A | 3/2000 | Salo et al. |
| 6,045,513 A | 4/2000 | Stone et al. |
| 6,049,730 A | 4/2000 | Kristbjarnarson |
| 6,052,620 A | 4/2000 | Gillberg et al. |
| 6,055,454 A | 4/2000 | Heemels |
| 6,064,910 A | 5/2000 | Andersson et al. |
| 6,076,014 A | 6/2000 | Alt |
| 6,076,015 A | 6/2000 | Hartley et al. |
| 6,084,253 A | 7/2000 | Turner, Jr. |
| 6,091,973 A | 7/2000 | Colla et al. |
| 6,101,416 A | 8/2000 | Sloman |
| 6,115,628 A | 9/2000 | Stadler et al. |
| 6,120,441 A | 9/2000 | Griebel |
| 6,126,611 A | 10/2000 | Bourgeois et al. |
| 6,128,534 A | 10/2000 | Park et al. |
| 6,128,535 A | 10/2000 | Maarse |
| 6,132,384 A | 10/2000 | Christopherson et al. |
| 6,134,473 A | 10/2000 | Hemming et al. |
| 6,141,581 A | 10/2000 | Olson et al. |
| 6,147,680 A | 11/2000 | Tareev |
| 6,148,230 A | 11/2000 | KenKnight |
| 6,148,234 A | 11/2000 | Struble |
| 6,163,724 A | 12/2000 | Hemming et al. |
| 6,169,921 B1 | 1/2001 | KenKnight et al. |
| 6,175,766 B1 | 1/2001 | Bornzin et al. |
| 6,190,326 B1 | 2/2001 | McKinnon et al. |
| 6,192,275 B1 | 2/2001 | Zhu et al. |
| 6,221,011 B1 | 4/2001 | Bardy |
| 6,226,551 B1 | 5/2001 | Zhu et al. |
| 6,227,072 B1 | 5/2001 | Ritchey et al. |
| 6,238,419 B1 | 5/2001 | Lindgren |
| 6,251,126 B1 | 6/2001 | Ottenhoff et al. |
| 6,253,102 B1 | 6/2001 | Hsu et al. |
| 6,258,039 B1 | 7/2001 | Okamoto et al. |
| 6,259,947 B1 | 7/2001 | Olson et al. |
| 6,266,554 B1 | 7/2001 | Hsu et al. |
| 6,270,457 B1 | 8/2001 | Bardy |
| 6,272,377 B1 | 8/2001 | Sweeney et al. |
| 6,275,731 B1 | 8/2001 | Zhu et al. |
| 6,277,072 B1 | 8/2001 | Bardy |
| 6,280,380 B1 | 8/2001 | Bardy |
| 6,280,462 B1 | 8/2001 | Hauser et al. |
| 6,282,440 B1 | 8/2001 | Brodnick et al. |
| 6,285,907 B1 | 9/2001 | Kramer et al. |
| 6,299,581 B1 | 10/2001 | Rapoport et al. |
| 6,312,378 B1 | 11/2001 | Bardy |
| 6,312,388 B1 | 11/2001 | Marcovecchio et al. |

| Patent | Date | Inventor |
|---|---|---|
| 6,324,421 B1 | 11/2001 | Stadler et al. |
| 6,324,427 B1 | 11/2001 | Florio |
| 6,336,903 B1 | 1/2002 | Bardy |
| 6,345,201 B1 | 2/2002 | Sloman et al. |
| 6,351,669 B1 | 2/2002 | Hartley et al. |
| 6,351,673 B1 | 2/2002 | Ding et al. |
| 6,353,759 B1 | 3/2002 | Hartley et al. |
| 6,358,203 B2 | 3/2002 | Bardy |
| 6,360,127 B1 | 3/2002 | Ding et al. |
| 6,363,270 B1 | 3/2002 | Colla et al. |
| 6,363,281 B1 | 3/2002 | Zhu et al. |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,393,316 B1 | 5/2002 | Gillberg et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,415,183 B1 | 7/2002 | Scheiner et al. |
| 6,418,340 B1 | 7/2002 | Conley et al. |
| 6,418,343 B1 | 7/2002 | Zhang et al. |
| 6,424,234 B1 | 7/2002 | Stevenson |
| 6,424,865 B1 | 7/2002 | Ding |
| 6,434,417 B1 | 8/2002 | Lovett |
| 6,434,428 B1 | 8/2002 | Sloman et al. |
| 6,438,409 B1 | 8/2002 | Malik et al. |
| 6,438,410 B2 | 8/2002 | Hsu et al. |
| 6,440,066 B1 | 8/2002 | Bardy |
| 6,449,503 B1 | 9/2002 | Hsu |
| 6,456,481 B1 | 9/2002 | Stevenson |
| 6,456,880 B1 | 9/2002 | Park et al. |
| 6,456,881 B1 | 9/2002 | Bornzin et al. |
| 6,459,929 B1 | 10/2002 | Hopper et al. |
| 6,466,820 B1 | 10/2002 | Juran et al. |
| 6,477,422 B1 | 11/2002 | Splett |
| 6,480,733 B1 | 11/2002 | Turcott |
| 6,480,734 B1 | 11/2002 | Zhang et al. |
| 6,487,443 B2 | 11/2002 | Olson et al. |
| 6,491,639 B1 | 12/2002 | Turcott |
| 6,493,586 B1 | 12/2002 | Stahmann et al. |
| 6,496,715 B1 | 12/2002 | Lee et al. |
| 6,505,067 B1 | 1/2003 | Lee et al. |
| 6,505,071 B1 | 1/2003 | Zhu et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,542,775 B2 | 4/2003 | Ding et al. |
| 6,553,259 B2 | 4/2003 | Mouchawar et al. |
| 6,564,106 B2 | 5/2003 | Guck et al. |
| 6,567,701 B2 | 5/2003 | Vonk |
| 6,574,507 B1 | 6/2003 | Bonnet |
| 6,589,188 B1 | 7/2003 | Street et al. |
| 6,595,927 B2 | 7/2003 | Pitts-Crick |
| 6,597,951 B2 | 7/2003 | Kramer et al. |
| 6,600,949 B1 | 7/2003 | Turcott |
| 6,607,509 B2 | 8/2003 | Bobroff et al. |
| 6,611,712 B2 | 8/2003 | Spinelli et al. |
| 6,615,082 B1 | 9/2003 | Mandell |
| 6,615,083 B2 | 9/2003 | Kupper |
| 6,615,089 B1 | 9/2003 | Russie et al. |
| 6,618,619 B1 | 9/2003 | Florio et al. |
| 6,622,046 B2 | 9/2003 | Fraley et al. |
| 6,631,290 B1 | 10/2003 | Guck et al. |
| 6,640,136 B1 | 10/2003 | Helland et al. |
| 6,641,542 B2 | 11/2003 | Cho et al. |
| 6,654,637 B2 | 11/2003 | Rouw et al. |
| 6,658,293 B2 | 12/2003 | Vonk |
| 6,684,100 B1 | 1/2004 | Sweeney et al. |
| 6,690,967 B2 | 2/2004 | Meij |
| 6,701,170 B2 | 3/2004 | Stetson |
| 6,708,058 B2 | 3/2004 | Kim et al. |
| 6,725,085 B2 | 4/2004 | Schwartzman et al. |
| 6,731,973 B2 | 5/2004 | Voith |
| 6,731,983 B2 | 5/2004 | Ericksen et al. |
| 6,731,984 B2 | 5/2004 | Cho et al. |
| 6,731,985 B2 | 5/2004 | Bradley et al. |
| 6,738,668 B1 | 5/2004 | Mouchawar et al. |
| 6,738,669 B1 | 5/2004 | Sloman et al. |
| 6,754,523 B2 | 6/2004 | Toole |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,768,923 B2 | 7/2004 | Ding et al. |
| 6,768,924 B2 | 7/2004 | Ding et al. |
| 6,772,008 B2 | 8/2004 | Zhu et al. |
| 6,773,404 B2 | 8/2004 | Poezevera et al. |
| 6,778,860 B2 | 8/2004 | Ostroff et al. |
| 6,782,291 B1 | 8/2004 | Bornzin |
| 6,788,974 B2 | 9/2004 | Bardy et al. |
| 6,830,548 B2 | 12/2004 | Bonnet et al. |
| 6,834,204 B2 | 12/2004 | Ostroff et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,881,192 B1 | 4/2005 | Park |
| 6,884,218 B2 | 4/2005 | Olson et al. |
| 6,885,893 B1 | 4/2005 | Lu |
| 6,888,538 B2 | 5/2005 | Ely et al. |
| 6,889,079 B2 | 5/2005 | Bocek et al. |
| 6,890,306 B2 | 5/2005 | Poezevera |
| 6,895,274 B2 | 5/2005 | Mower |
| 6,904,315 B2 | 6/2005 | Panken et al. |
| 6,904,320 B2 | 6/2005 | Park et al. |
| 6,915,160 B2 | 7/2005 | Auricchio et al. |
| 6,915,164 B2 | 7/2005 | Bradley et al. |
| 6,917,832 B2 | 7/2005 | Hutten et al. |
| 6,925,324 B2 | 8/2005 | Shusterman |
| 6,925,330 B2 | 8/2005 | Kleine |
| 6,927,721 B2 | 8/2005 | Ostroff |
| 6,928,324 B2 | 8/2005 | Park et al. |
| 6,937,907 B2 | 8/2005 | Bardy et al. |
| 6,944,495 B2 | 9/2005 | MacAdam et al. |
| 6,944,579 B2 | 9/2005 | Shimizu |
| 6,950,702 B2 | 9/2005 | Sweeney |
| 6,950,705 B2 | 9/2005 | Bardy et al. |
| 6,952,608 B2 | 10/2005 | Ostroff |
| 6,952,610 B2 | 10/2005 | Ostroff |
| 6,954,670 B2 | 10/2005 | Ostroff |
| 6,959,214 B2 | 10/2005 | Pape et al. |
| 6,961,613 B2 | 11/2005 | Bjorling et al. |
| 6,961,619 B2 | 11/2005 | Casey |
| 6,973,350 B1 | 12/2005 | Levine et al. |
| 6,975,904 B1 | 12/2005 | Sloman |
| 6,978,178 B2 | 12/2005 | Sommer et al. |
| 6,983,264 B2 | 1/2006 | Shimizu |
| 6,988,003 B2 | 1/2006 | Bardy et al. |
| 6,993,379 B1 | 1/2006 | Kroll |
| 6,993,389 B2 | 1/2006 | Ding et al. |
| 6,999,817 B2 | 2/2006 | Park et al. |
| 7,006,869 B2 | 2/2006 | Bradley |
| 7,025,730 B2 | 4/2006 | Cho et al. |
| 7,027,861 B2 | 4/2006 | Thompson |
| 7,027,868 B2 | 4/2006 | Rueter et al. |
| 7,027,871 B2 | 4/2006 | Burnes et al. |
| 7,031,773 B1 | 4/2006 | Levine et al. |
| 7,039,459 B2 | 5/2006 | Bardy |
| 7,039,465 B2 | 5/2006 | Bardy |
| 7,043,299 B2 | 5/2006 | Erlinger |
| 7,050,851 B2 | 5/2006 | Plombon et al. |
| 7,062,327 B2 | 6/2006 | Bradley et al. |
| 7,065,400 B2 | 6/2006 | Schechter |
| 7,065,407 B2 | 6/2006 | Bardy |
| 7,065,410 B2 | 6/2006 | Bardy et al. |
| 7,069,080 B2 | 6/2006 | Bardy |
| 7,076,296 B2 | 7/2006 | Rissmann et al. |
| 7,079,988 B2 | 7/2006 | Albera |
| 7,081,095 B2 | 7/2006 | Lynn et al. |
| 7,085,599 B2 | 8/2006 | Kim et al. |
| 7,090,682 B2 | 8/2006 | Sanders et al. |
| 7,092,754 B2 | 8/2006 | Bardy et al. |
| 7,094,207 B1 | 8/2006 | Koh |
| 7,096,064 B2 | 8/2006 | Deno et al. |
| 7,103,404 B2 | 9/2006 | Staler et al. |
| 7,107,093 B2 | 9/2006 | Burnes |
| 7,113,823 B2 | 9/2006 | Yonce et al. |
| 7,115,097 B2 | 10/2006 | Johnson |

| | | |
|---|---|---|
| 7,117,036 B2 | 10/2006 | Florio |
| 7,120,495 B2 | 10/2006 | Bardy et al. |
| 7,123,960 B2 | 10/2006 | Ding |
| 7,127,290 B2 | 10/2006 | Girouard |
| 7,129,935 B2 | 10/2006 | Mackey |
| 7,139,610 B2 | 11/2006 | Ferek-Petric |
| 7,144,586 B2 | 12/2006 | Levy et al. |
| 7,146,212 B2 | 12/2006 | Bardy et al. |
| 7,149,575 B2 | 12/2006 | Ostroff et al. |
| 7,155,278 B2 | 12/2006 | King et al. |
| 7,160,252 B2 | 1/2007 | Cho |
| 7,177,689 B2 | 2/2007 | Ternes et al. |
| 7,179,229 B1 | 2/2007 | Koh |
| 7,181,285 B2 | 2/2007 | Lindh |
| 7,184,835 B2 | 2/2007 | Kramer et al. |
| 7,191,003 B2 | 3/2007 | Greenhut et al. |
| 7,191,004 B2 | 3/2007 | Kim et al. |
| 7,194,302 B2 | 3/2007 | Bardy et al. |
| 7,194,309 B2 | 3/2007 | Ostroff et al. |
| 7,194,313 B2 | 3/2007 | Libbus |
| 7,203,540 B2 | 4/2007 | Ding et al. |
| 7,203,542 B2 | 4/2007 | Obel |
| 7,203,543 B2 | 4/2007 | Meyer et al. |
| 7,212,862 B2 | 5/2007 | Park et al |
| 7,225,021 B1 | 5/2007 | Park et al. |
| 7,228,173 B2 | 6/2007 | Cazares |
| 7,233,821 B2 | 6/2007 | Hettrick et al. |
| 7,236,819 B2 | 6/2007 | Brockway |
| 7,242,978 B2 | 7/2007 | Cao |
| 7,245,962 B2 | 7/2007 | Ciaccio et al. |
| 7,248,921 B2 | 7/2007 | Palreddy et al. |
| 7,248,925 B2 | 7/2007 | Bruhns et al. |
| 7,263,399 B2 | 8/2007 | Carlson |
| 7,277,754 B2 | 10/2007 | McCabe et al. |
| 7,286,876 B2 | 10/2007 | Yonce et al. |
| 7,299,086 B2 | 11/2007 | McCabe et al. |
| 7,299,093 B2 | 11/2007 | Zhu et al. |
| 7,308,311 B2 | 12/2007 | Sorensen |
| 7,319,900 B2 | 1/2008 | Kim et al. |
| 7,330,761 B2 | 2/2008 | Zhang |
| 7,337,000 B2 | 2/2008 | Meyer et al. |
| 7,359,749 B2 | 4/2008 | Quenet et al. |
| 7,369,889 B2 | 5/2008 | Astrom et al. |
| 7,392,086 B2 | 6/2008 | Sathaye |
| 7,426,412 B1 | 9/2008 | Schecter |
| 7,438,686 B2 | 10/2008 | Cho |
| 7,457,664 B2 | 11/2008 | Zhang et al. |
| 7,463,924 B2 | 12/2008 | Bardy et al. |
| 7,468,040 B2 | 12/2008 | Hartley |
| 7,477,932 B2 | 1/2009 | Lee |
| 7,499,751 B2 | 3/2009 | Meyer et al. |
| 7,509,170 B2 | 3/2009 | Zhang et al. |
| 7,519,423 B2 | 4/2009 | Begemann et al. |
| 7,558,628 B2 | 7/2009 | Yonce et al. |
| 7,580,741 B2 | 8/2009 | Cazares et al. |
| 7,587,240 B2 | 9/2009 | Zhang et al. |
| 7,617,002 B2 | 11/2009 | Goetz |
| 7,647,108 B2 | 1/2010 | Freeberg |
| 7,653,431 B2 | 1/2010 | Cazares et al. |
| 7,680,536 B2 | 3/2010 | Sathaye et al. |
| 7,684,861 B2 | 3/2010 | Sanders |
| 7,706,866 B2 | 4/2010 | Zhang et al. |
| 7,734,347 B2 | 6/2010 | Sathaye et al. |
| 7,738,959 B2 | 6/2010 | Manrodt et al. |
| 7,761,162 B2 | 7/2010 | Dong et al. |
| 2002/0002327 A1 | 1/2002 | Grant et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0052631 A1* | 5/2002 | Sullivan et al. .................. 607/7 |
| 2002/0082658 A1 | 6/2002 | Heinrich et al. |
| 2002/0095184 A1 | 7/2002 | Bardy et al. |
| 2002/0107544 A1 | 8/2002 | Ostroff et al. |
| 2002/0107545 A1 | 8/2002 | Rissmann et al. |
| 2002/0143264 A1 | 10/2002 | Ding et al. |
| 2003/0023175 A1 | 1/2003 | Arzbaecher et al. |
| 2003/0083708 A1 | 5/2003 | Bradley et al. |
| 2003/0135248 A1* | 7/2003 | Stypulkowski ................. 607/73 |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0212436 A1 | 11/2003 | Brown |
| 2004/0064162 A1 | 4/2004 | Manrodt et al. |
| 2004/0082975 A1 | 4/2004 | Meyer et al. |
| 2004/0116971 A1 | 6/2004 | Bjorling et al. |
| 2004/0116978 A1* | 6/2004 | Bradley ........................ 607/48 |
| 2004/0133248 A1* | 7/2004 | Frei et al. ...................... 607/45 |
| 2004/0172065 A1 | 9/2004 | Sih et al. |
| 2004/0215253 A1 | 10/2004 | Weinberg |
| 2004/0215277 A1 | 10/2004 | Oosterhoff et al. |
| 2004/0230229 A1 | 11/2004 | Lovett et al. |
| 2004/0260351 A1 | 12/2004 | Holmstrom et al. |
| 2005/0004612 A1 | 1/2005 | Scholten et al. |
| 2005/0010120 A1 | 1/2005 | Jung |
| 2005/0038478 A1 | 2/2005 | Klepfer et al. |
| 2005/0043652 A1 | 2/2005 | Lovett et al. |
| 2005/0060002 A1 | 3/2005 | Zhu et al. |
| 2005/0060007 A1 | 3/2005 | Goetz |
| 2005/0065587 A1 | 3/2005 | Gryzwa |
| 2005/0085865 A1 | 4/2005 | Tehrani |
| 2005/0113710 A1 | 5/2005 | Stahmann et al. |
| 2005/0131477 A1 | 6/2005 | Meyer et al. |
| 2005/0131478 A1 | 6/2005 | Kim et al. |
| 2005/0143785 A1 | 6/2005 | Libbus |
| 2006/0069322 A1 | 3/2006 | Zhang et al. |
| 2006/0074331 A1 | 4/2006 | Kim et al. |
| 2006/0111747 A1 | 5/2006 | Cazares et al. |
| 2006/0116593 A1 | 6/2006 | Zhang et al. |
| 2006/0129193 A1 | 6/2006 | Zhang |
| 2006/0129194 A1 | 6/2006 | Zhang |
| 2006/0129195 A1 | 6/2006 | Sathaye et al. |
| 2006/0129196 A1 | 6/2006 | Dong et al. |
| 2006/0129197 A1 | 6/2006 | Zhang et al. |
| 2006/0129198 A1 | 6/2006 | Zhang et al. |
| 2006/0129199 A1 | 6/2006 | Zhang et al. |
| 2006/0241711 A1* | 10/2006 | Sathaye ........................ 607/28 |
| 2006/0247693 A1 | 11/2006 | Dong |
| 2006/0247695 A1 | 11/2006 | Stalsberg et al. |
| 2006/0253043 A1 | 11/2006 | Zhang et al. |
| 2006/0253044 A1 | 11/2006 | Zhang et al. |
| 2007/0049974 A1 | 3/2007 | Li et al. |
| 2007/0055124 A1 | 3/2007 | Viswanathan et al. |
| 2007/0142741 A1 | 6/2007 | Berthon-Jones et al. |
| 2007/0239057 A1 | 10/2007 | Pu et al. |
| 2007/0255321 A1 | 11/2007 | Gerber et al. |
| 2008/0004665 A1 | 1/2008 | McCabe et al. |
| 2008/0009909 A1 | 1/2008 | Sathaye et al. |
| 2008/0046019 A1 | 2/2008 | Sathaye et al. |
| 2008/0071318 A1 | 3/2008 | Brooke et al. |
| 2008/0234556 A1 | 9/2008 | Brooke et al. |
| 2008/0275522 A1 | 11/2008 | Dong |
| 2008/0294215 A1 | 11/2008 | Sathaye |
| 2008/0300644 A1 | 12/2008 | Sathaye |
| 2009/0030470 A1* | 1/2009 | Holmstrom et al. ............ 607/27 |
| 2009/0043351 A1 | 2/2009 | Sathaye |
| 2009/0043352 A1 | 2/2009 | Brooke et al. |

FOREIGN PATENT DOCUMENTS

| | | |
|---|---|---|
| EP | 0560569 | 9/1993 |
| EP | 0940155 | 9/1999 |
| EP | 1038498 | 9/2000 |
| EP | 1151718 | 11/2001 |
| EP | 1291038 | 3/2003 |
| EP | 1629863 | 3/2006 |
| WO | WO9217240 | 10/1992 |
| WO | WO9220402 | 11/1992 |
| WO | WO9904841 | 4/1999 |
| WO | WO001438 | 1/2000 |
| WO | WO017615 | 3/2000 |
| WO | WO0240097 | 5/2002 |
| WO | WO0247761 | 6/2002 |
| WO | WO02087696 | 11/2002 |
| WO | WO03003905 | 1/2003 |
| WO | WO03028550 | 4/2003 |
| WO | WO2004026398 | 4/2004 |
| WO | WO2004091720 | 10/2004 |
| WO | WO2005058412 | 6/2005 |

| | | |
|---|---|---|
| WO | WO2005089865 | 9/2005 |
| WO | WO2006065707 | 6/2006 |
| WO | WO2007087025 | 8/2007 |
| WO | WO2008005270 | 1/2008 |
| WO | WO2009020639 | 2/2009 |

OTHER PUBLICATIONS

U.S. Appl. No. 11/114,569, filed Apr. 26, 2005, Sathaye.
U.S. Appl. No. 11/890,668, filed Aug. 7, 2007, Sathaye et al.
Splett et al. "Determination of Pacing Capture in Implantable Defibrillators: Benefit of Evoked Response Detection Using RV Coil to Can Vector," PACE, vol. 23, pp. 1645-1650.
Acar et al., SVD-based on-line exercise ECG signal orthogonalization, IEEE Transactions on Biomedical Engineering, vol. 46, No. 3, Mar. 1999. Abstract only.
Ajilore et al., Nightcap: Laboratory and home-based evaluation of a portable sleep monitor, 32 Psychophysiology, 32-98, 1995. Abstract only.
Belouchrani et al., Blind Source Separation Based on Time-Frequency Signal Representations, IEEE Transactions on Signal Processing, vol. 46, No. 11, pp. 2888-2897, Nov. 1998.
Cohen et al. Capture Management Efficacy in children and young adults with endocardial and unipolar epicardial systems. Europace, vol. 6, pp. 248-255, 2004.
Comon, Independent component analysis, a new concept?, Signal Processing, vol. 36, No. 3, pp. 287-314, Apr. 1994.
Gallois et al., Multi-Channel Analysis of the EEG Signals and Statistic Particularities for Epileptic Seizure Forecast, Second Joint EMBS/BMES Conference, pp. 208-215, Oct. 23-26, 2002.
Gradaus et al., Nonthoracotomy Implantable Cardioverter Defibrillator Placement in Children: Use of a Subcutaneous Array Leads and Abdominally Placed Implantable Cardioverter Defibrillators in Children, Journal of Cardiovascular Electrophysiology, vol. 12, No. 3, pp. 356-360, Mar. 2001.
Hartz et al., New Approach to Defibrillator Insertion, Journal of Thoracic Cardiovascular Surgery, vol. 97, pp. 920-922, 1989.
Hyvärinen et al., Independent Component Analysis: A Tutorial, Helsinki University of Technology, Apr. 1999.
Kolettis et al., Submammary Implantation of a Cardioverter-Defibrillator with a Nonthoracotomy Lead System, American Heart Journal, vol. 126, pp. 1222-1223, Nov. 1993.
Krahn et al., Recurrent syncope. Experience with an implantable loop record, Cardiol. Clin., vol. 15(2), pp. 316-326, May 1997.
Leng et al., "Lead Configuration for Defibrillator Implantation in a Patient with Congenital Heart Disease and a Mechanical Prosthetic Tricuspid Valve", PACE, vol. 24, No. 8, pp. 1291-1292, Aug. 2001.
Park et al., Use of an Implantable Cardioverter Defibrillator in an Eight-Month-Old Infant with Ventricular Fibrillation Arising from a Myocardial Fibroma, PACE, vol. 22, No. 1, pp. 138-139, Jan. 1999.
Rieta, et al., Atrial Activity Extraction Based on Blind Source Separation as an Alternative to QRST Cancellation for Atrial Fibrillation Analysis, Computers in Cardiology, vol. 27, pp. 69-72, 2000.
Schuder et al., Experimental Ventricular Defibrillation with an Automatic and Completely Implanted System, Trans. American Society Artif. Int. Organs, vol. 16, pp. 207-212, 1970.
Schuder et al., Transthoracic Ventricular Defibrillation in the Dog with Truncated and Untruncated Exponential Stimuli, IEEE Transitions on Bio-Medical Engineering, vol. BME-18, No. 6, pp. 410-415, Nov. 1971.
Schuder et al., Ventricular Defibrillation in the Dog Using Implanted and Partially Implanted Electrode Systems, American Journal of Cardiology, vol. 33, pp. 243-247, Feb. 1974.
Smits et al., Defibrillation Threshold (DFT) Model of a Fully Subcutaneous ICD System, Europace Supplements, vol. 2, Jun. 2001 at column 778, p. B83.
Stirbis et al., Optimizing of the Shape of Implanted Artificial Pacemakers, Kaunas Medical Institute, Translated from Meditsinskaya Tekhnika, No. 6, pp. 25-27, 1986.
Verrier et al., Sleep, dreams, and sudden death: the case for sleep as an autonomic stress test for the heart, 31 Cardiovascular Research 181-211, 1996.
Verrier et al., Sleep Related Cardiovascular Risk: New Home-Based Monitoring Technology for Improved Diagnosis and Therapy, 2 A.N. E. 158-175, 1997.
Waldemark et al., Detection of Apnea using Short Window FFT Technique and Artificial Neural Network, 3390 SPIE International Society for Optical Engineering 122-133, 1998. Partial article.
Zarzoso et al., Blind Separation of Independent Sources for Virtually Any Source Probability Density Function, IEEE Transactions on Signal Processing, vol. 47, No. 9, pp. 2419-2432, Sep. 1999.
Zarzoso et al., Noninvasive Fetal Electrocardiogram Extraction: Blind Separation Versus Adaptive Noise Cancellation, IEEE Transactions on Biomedical Engineering, vol. 48, No. 1, pp. 12-18, Jan. 2001.
Office Action dated Apr. 17, 2007 from U.S. Appl. No. 11/114,569, 11 pages.
Office Action Response dated Aug. 17, 2007 from U.S. Appl. No. 11/114,569, 9 pages.
Office Action dated Nov. 14, 2007 from U.S. Appl. No. 11/114,569, 13 pages.
Office Action Response dated Jan. 14, 2008 from U.S. Application No. 11/114,569, 8 pages.
Notice of Allowance dated Feb. 14, 2008 from U.S. Appl. No. 11/114,569, 4 pages.
Office Action dated Nov. 9, 2007 from U.S. Appl. No. 10/955,393, 13 pages.
Office Action Response dated Apr. 21, 2008 from U.S. Appl. No. 10/955,393, 12 pages.
Office Action dated Jul. 31, 2008 from U.S. Appl. No. 10/955,393, 8 pages.
Office Action Response dated Dec. 22, 2008 from U.S. Appl. No. 10/955,393, 9 pages.
Office Action dated Mar. 20, 2009 from U.S. Appl. No. 10/955,393, 10 pages.
Office Action Response dated Jun. 9, 2009 from U.S. Appl. No. 10/955,393, 10 pages.
Notice of Allowance dated Sep. 2, 2009 from U.S. Appl. No. 10/955,393, 4 pages.
Office Action dated Mar. 28, 2007 from U.S. Appl. No. 11/116,558, 13 pages.
Office Action Response dated Sep. 28, 2007 from U.S. Appl. No. 11/116,558, 15 pages.
Office Action Response dated Oct. 29, 2007 from U.S. Appl. No. 11/116,558, 7 pages.
Office Action dated Mar. 6, 2008 from U.S. Appl. No. 11/116,558, 14 pages.
Office Action Response dated May 6, 2008 from U.S. Appl. No. 11/116,558, 11 pages.
Office Action dated May 28, 2008 from U.S. Appl. No. 11/116,558, 3 pages.
International Search Report and Written Opinion dated Dec. 12, 2008 from PCT Application No. PCT/US2008/009488, 14 pages.
International Preliminary Report on Patentability dated Feb. 18, 2010 from PCT Application No. PCT/US2008/009488, 7 pages.
International Search Report and Written Opinion dated Apr. 6, 2009 from PCT Application No. PCT/US2009/033687, 16 pages.
File history from Sep. 1, 2010-Oct. 31, 2010 for U.S. Appl. No. 11/890,668 retrieved from USPTO System on Nov. 1, 2010, 19 pages.
File history for U.S. Appl. No. 11/890,668 as retrieved from U.S. Patent and Trademark System on Jan. 21, 2011, 234 pages.
File history for U.S. Appl. No. 12/154,410 as retrieved from U.S. Patent and Trademark System on Dec. 28, 2011, 213 pages.
File history for U.S. Appl. No. 12/154,411 as retrieved from U.S. Patent and Trademark Office Pair System on Dec. 28, 2011, 181 pages.
File history for U.S. Appl. No. 11/890,668 as retrieved from U.S. Patent and Trademark System on Dec. 28, 2011, 337 pages.
File history for U.S. Appl. No. 12/217,652 as retrieved from U.S. Patent and Trademark System on Dec. 28, 2011, 191 pages.
File history for U.S. Appl. No. 12/220,496 as retrieved from U.S. Patent and Trademark System on Dec. 28, 2011, 221 pages.

File history for U.S. Appl. No. 12/368,828 as retrieved from U.S. Patent and Trademark System on Dec. 28, 2011, 191 pages.

File history for U.S. Appl. No. 11/890,668 as retrieved from U.S. Patent and Trademark System on Jul. 18, 2011, 269 pages.

File history for U.S. Appl. No. 12/217,652 as retrieved from U.S. Patent and Trademark System on Jul. 18, 2011, 154 pages.

File history for EP Application No. 08795112.5 as retrieved from the European Patent Office electronic file system on Jul. 18, 2011, 140 pages.

Office Action dated May 13, 2011 from Australian Application No. 2008284265, 3 pages.

* cited by examiner

THERAPEUTIC ELECTRICAL STIMULATION THAT AVOIDS UNDESIRABLE ACTIVATION

FIELD OF THE INVENTION

The present invention relates generally to methods and devices for determining energy parameters for therapeutic electrical stimulation that produce a desired activation and avoid an undesirable activation.

BACKGROUND OF THE INVENTION

When functioning normally, the heart produces rhythmic contractions and is capable of pumping blood throughout the body. The heart has specialized conduction pathways in both the atria and the ventricles that enable excitation impulses (i.e. depolarizations) initiated from the sino-atrial (SA) node to be rapidly conducted throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management (CRM) devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart and/or attached to the heart are coupled to electrodes that sense the heart's electrical signals and deliver stimulation to the heart in accordance with various therapies for treating cardiac arrhythmias and dysynchronies.

Pacemakers are CRM devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to "capture" the heart tissue by generating a propagating depolarization wave that results in a contraction of the heart chamber. It is desirable for a pace pulse to have sufficient energy to capture the heart chamber without expending energy significantly in excess of the capture threshold.

If the pace pulse energy is too low, the pace pulses may not reliably produce a contractile response in the heart chamber, resulting in ineffective pacing. If the pace pulse energy is too high, the pacing pulses produce capture, but may also inadvertently stimulate the heart in an undesirable mode or may undesirably stimulate other body structures. The present invention provides an approach for determining energy parameters for cardiac pacing and/or other therapeutic electrical stimulation that produces a desired activation, such as capture, and avoids undesirable activation.

SUMMARY OF THE INVENTION

The present invention involves approaches for determining the energy for therapeutic electrical stimulation that avoids undesirable activation. One embodiment of the invention is directed to a method implementable in a medical device for determining energy parameters for a therapeutic electrical stimulation. A strength-duration relationship for at least one desired activation produced by the therapeutic electrical stimulation is measured. A strength-duration relationship for at least one undesirable activation produced by the therapeutic electrical stimulation is provided. The medical device selects, based on the desired and undesirable strength-duration relationships, one or more energy parameters for the therapeutic electrical stimulation that produce the desired activation and avoid the undesirable activation.

For example, the strength-duration relationship for the desired activation may comprise a strength-duration relationship for capture of a heart by pacing pulses delivered to the heart. Measuring the strength-duration relationship for the desired activation may involve automatically measuring the strength-duration relationship for capture. In one approach, providing the strength-duration relationship for the undesirable activation may involve providing an amplitude threshold for undesirable activation. In another approach, the strength-duration relationship for undesirable activation may be provided by measuring the strength-duration relationship for the undesirable activation for a particular patient. In a further approach, the strength-duration relationship for undesirable activation may be determined based on theoretical analysis. In yet another approach, the strength-duration curve for the undesirable activation may be determined based on population data.

The strength-duration relationship for the desired activation and/or the undesirable activation may comprise multiple-point strength-duration curves. The energy parameters may be selected from a region between the desired activation strength-duration curve and the undesirable activation strength-duration curve.

In one scenario, the desired activation may comprise capture and the undesirable activation may comprise nerve activation, e.g., phrenic nerve activation, and/or skeletal muscle activation. In another scenario, the desired activation may involve cardiac capture at a cathodal pacing site and the undesirable activation may involve cardiac capture at an anodal pacing site.

According to one implementation, the strength-duration relationship for the desired activation is determined by performing a test to determine a capture amplitude threshold for cardiac pacing. An amplitude threshold for the undesirable activation is provided. The capture amplitude threshold is compared during a capture threshold test to the undesirable activation threshold. One or more test energy parameters, such as stimulation pulse width and/or stimulation pulse amplitude, are modified based on the comparison. The energy parameters for the therapeutic electrical stimulation are selected based on the modified test energy parameters.

According to one implementation, the amplitude of the test stimulation pulse may be set to the amplitude threshold of undesirable activation or the amplitude threshold of undesirable activation adjusted by a predetermined margin.

In some embodiments, an alert may be generated if the selected energy parameters for the therapeutic electrical stimulation exceed the strength-duration relationship for undesirable activation.

Another embodiment of the invention involves a therapy device which may be an implantable device. The therapy device includes electrodes configured to deliver therapeutic electrical stimulation. Device circuitry measures a strength-duration relationship for at least one desired activation. A therapy control processor configured to select, based on the strength-duration relationship for the desired activation and a strength-duration relationship for at least one undesirable activation, energy parameters for the therapeutic electrical stimulation that produces the desired activation and avoids the undesirable activation.

According to one implementation, the electrodes of the device are electrically coupled to a heart and the therapeutic electrical stimulation involves pacing pulses delivered to the heart. Capture circuitry is configured to measure the strength-duration relationship for capture of the heart. The therapy control processor selects, based on the strength-duration relationship for capture and the strength-duration relationship for the undesirable activation, energy parameters for the pacing pulses that produce capture of the heart and avoid undesirable activation.

For example, the therapy control processor may select the energy parameters for the therapeutic electrical stimulation based on a region defined by the strength-duration curve for the desired activation and the strength-duration curve for the undesirable activation.

The strength-duration relationship of the desired activation may comprise a cardiac capture amplitude threshold which is measured by measurement circuitry during a capture threshold test. The therapy processor compares the capture amplitude threshold determined by the test to an undesirable activation amplitude threshold. At least one test energy parameter is modified based on the comparison.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
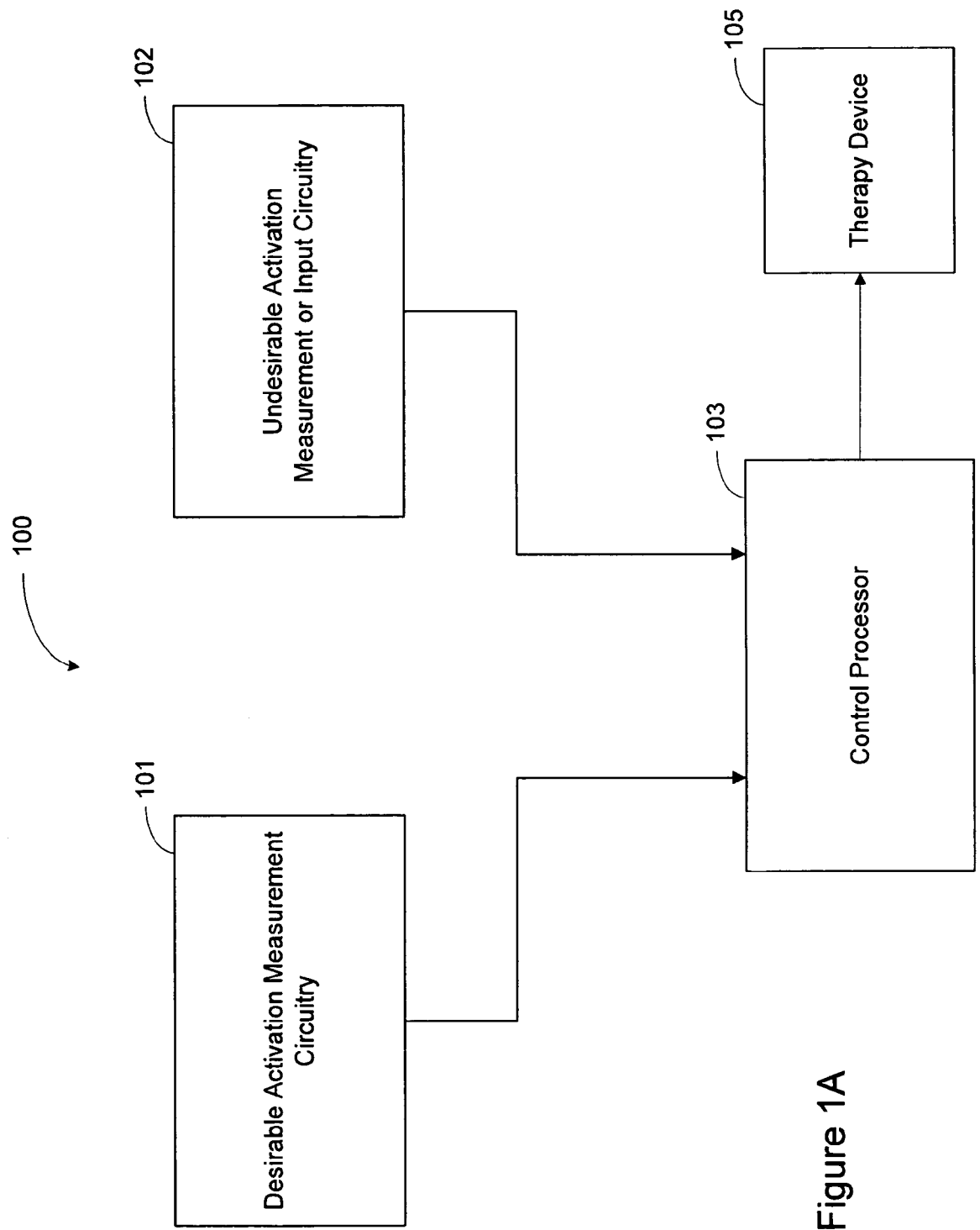
FIG. 1A is a block diagram of a system for selecting energy parameters for therapeutic electrical stimulation in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Implantable devices have been used to deliver therapeutic electrical stimulation to treat patients suffering from various disorders. For example, electrical stimulation of the hypoglossal nerve has been used as therapy for sleep apnea, electrical stimulation of baroreceptors has been used as therapy for hypertension, electrical stimulation of the vagal nerve has been suggested for treatment of depression, obesity, and epilepsy. In addition, electrical stimulation of the heart has been used to provide therapy for anomalies of cardiac rhythm or synchronization.

Methods and devices described herein are directed to an approach for selecting energy parameters for the delivery of therapeutic electrical stimulation. Electrical stimulation delivered to one body structure to produce a desired therapeutic activation may undesirably cause activation of another body structure. According to various embodiments, appropriate selection of the energy parameters that produce the desired activation and avoid the undesirable activation involves the use of strength-duration relationships measured or otherwise provided for the desired activation and the undesirable activation. According to various aspects of the invention, the selection of energy parameters may involve selection of one or more of pulse width, pulse amplitude, frequency, duty cycle, pulse geometry, and/or other energy parameters. Some embodiments provided herein are described within the context of selecting the energy parameters pulse amplitude and pulse width for cardiac pacing. However, it will be appreciated that the techniques for selecting energy parameters in accordance with these examples may be extended to any of type of energy parameter, any type of therapeutic electrical stimulation, and/or any type of undesirable activation.

For example, in one implementation, the desired activation involves cardiac capture and the undesirable activation involves nerve and/or muscle activation. In another implementation, the desired activation involves nerve activation and the undesirable activation involves muscle activation. Various other combinations of desired and undesirable activations are considered to be within the scope of the present invention.

FIG. 1A depicts a block diagram of a system 100 that may be used to determine the energy parameters, i.e., strength and duration, of electrical stimulation pulses for therapeutic stimulation in accordance with embodiments of the invention. The system includes circuitry 101 configured to measure the strength-duration relationship for at least one desirable activation. For example, the circuitry 101 may automatically or semi-automatically perform a test to determine strength-duration parameters of electrical stimulation pulses that produce a desired activation. The strength-duration relationship so measured may comprise one point or multiple points of the desired activation strength-duration relationship. One example of a desirable activation comprises cardiac capture, although activation of various nerves and muscles by electrical stimulation has been used for various therapeutic purposes. For example, activation of the hypoglossal nerve has been used as a treatment for sleep apnea as described in U.S. Pat. No. 5,591,216 which is incorporated herein by reference. Electrical activation of baroreceptors has been used for treatment of hypertension and/or to reduce myocardial ischemic damage as described in commonly owned U.S. Patent Publication 20050143785 which is incorporated herein by reference.

The system 100 includes circuitry 102 configured to measure or otherwise provide the strength-duration relationship for one or more undesirable activations. The strength and duration parameters of electrical stimulation that causes undesirable stimulation may be provided by various methods. In one example, the circuitry 102 may involve communication circuitry having a user interface configured to input strength and duration parameters for undesirable activation from an external device. In another example, the circuitry 102 may be configured to measure the strength and/or duration of electrical stimulation pulses that produce the undesirable stimulation.

In various implementations, the undesirable activation may comprise skeletal muscle activation, undesirable modes of cardiac activation, and/or undesirable nerve activation. Commonly owned U.S. Pat. No. 6,772,008, which is incorporated herein by reference, describes methods and systems that may be used in relation to measuring undesirable skeletal muscle activation. Skeletal muscle activation may be measured, for example, through the use of an accelerometer and/or other circuitry that senses accelerations indicating muscle movements that coincide with the output of the stimulation pulse.

Other methods of measuring skeletal muscle activation may involve, for example, the use of an electromyogram sensor (EMG), microphone, and/or other sensors. In one implementation, activation of the laryngeal muscles may be automatically detected using a microphone to detect the patient's coughing response to undesirable activation of the laryngeal muscles due to electrical stimulation. A relationship between the coughing response and the energy parameters of electrical stimulation may be determined during a test which can be performed on command or automatically by the measurement circuitry 102.

In another implementation, the relationship between the coughing response and laryngeal muscle activation may be detected by a listener who assists in determining the strength-duration relationship of the undesirable stimulation during a test. The strength-duration relationship determined with the assistance of the listener may be input to the system via input circuitry 102 coupled to the control processor 103.

Undesirable nerve activation may be detected by sensing a parameter that is directly or indirectly responsive to the nerve activation. Undesirable nerve activation, such as activation of the vagus or phrenic nerves, for example, may be directly sensed using electroneurogram (ENG) electrodes and circuitry to measure and/or record nerve spikes and/or action potentials in a nerve. An ENG sensor may comprise a neural cuff and/or other type or neural electrodes located on or near the nerve of interest. For example, systems and methods for direct measurement of nerve activation signals are discussed in U.S. Pat. Nos. 4,573,481 and 5,658,318 which are incorporated herein by reference. The ENG may comprise a helical neural electrode that wraps around the nerve and is electrically connected to circuitry configured to measure the nerve activity. The neural electrodes and circuitry operate to detect an electrical activation (action potential) of the nerve following application of the electrical stimulation pulse.

In another approach, neural activation is detected by sensing a surrogate parameter that is indirectly responsive to nerve stimulation. Blood pressure and heart rate are two examples of parameters that change responsive to stimulation of the vagus nerve. In some embodiments, a patient's blood pressure and/or heart rate may be measured during and/or closely following delivery of electrical stimulation. The detected change in blood pressure and/or heart rate may be related to activation of the vagus nerve.

Values from the desirable activation measurement circuitry 101 and the undesirable activation circuitry 102 are provided to a control processor 103. The control processor 103 determines, from the strength-duration relationship of the desirable activation and the strength-duration relationship of the undesirable activation, the energy parameters for therapeutic electrical stimulation pulses. Control signals developed by the control processor 103 may be used to control electrical stimulation pulses produced by a therapy device 105 and delivered to a patient.

Cardiac rhythm management (CRM) devices typically include multiple pacing electrodes disposed in, on, or about the heart. For example, the electrodes may be disposed within or on a single heart chamber and/or within or on multiple heart chambers. In bipolar pacing of a heart chamber, electrodes used for delivery of pacing pulses include one or more cathode electrodes and one or more anode electrodes disposed within or on the heart chamber. Typically, pacing energy is delivered to the heart tissue via the cathode electrode(s) with a return path provided via the anode electrode(s). If capture occurs, the energy injected at the cathode electrode site creates a propagating wavefront of depolarization that triggers a contraction of the cardiac muscle.

Undesirable cardiac stimulation modes and/or stimulation of extra-cardiac structures constrains the energy level used for pacing pulses. For example, pacing at excessive energy levels may cause the cardiac tissue to be stimulated at the site of the anode electrode instead of the cathode electrode as expected. Cardiac signals sensed following the pacing pulse are analyzed to determine if a pacing pulse captured the cardiac tissue. Capture via anodal activation may result in erroneous detection of capture or loss of capture.

In some scenarios, excessive pacing levels may cause undesirable activation of extracardiac nerve or muscle tissues. For example, left ventricular pacing at energy levels exceeding a threshold level may cause undesirable activation of the diaphragm and/or phrenic nerve.

Figure 1B:
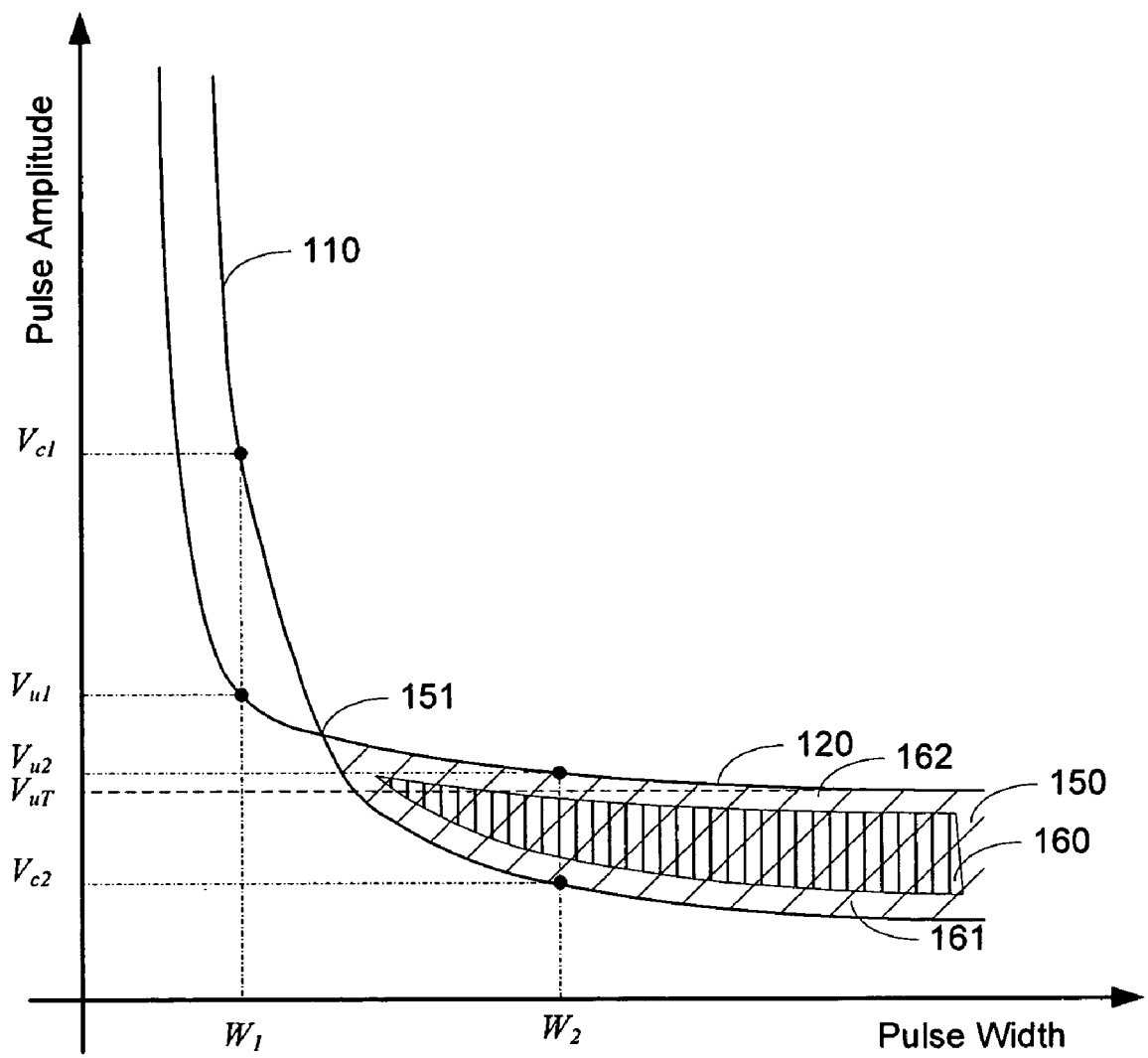
FIG. 1B is a graph illustrating various aspects of a strength-duration plot for a desired activation and a strength-duration plot for an undesirable activation that may be used to determine energy parameters for a therapeutic electrical stimulation in accordance with embodiments of the invention.

Capture is produced by pacing pulses having sufficient energy to produce a propagating wavefront of electrical depolarization that results in a contraction of the heart tissue. The energy of the pacing pulse is a product of two energy parameters the amplitude of the pacing pulse and the duration of the pulse. Thus, the capture threshold voltage over a range of pulse widths may be expressed in a strength-duration plot 110 as illustrated in FIG. 1B. A CRM device, such as a pacemaker, may have the capability to adjust the pacing pulse energy by modifying either or both the pulse energy and the pulse amplitude to produce capture.

Undesirable activation by a pacing pulse is also dependent on the pulse energy. The strength-duration plot 120 for undesirable activation may have a different characteristic from the capture strength-duration and may have a relationship between pacing pulse voltage and pacing pulse width.

FIG. 1B provides graphs illustrating a strength-duration plot 110 associated with capture and a strength-duration plot 120 associated with an undesirable activation. A pacing pulse having a pulse width of $W_1$ requires a pulse amplitude of $V_{c1}$ to produce capture. A pacing pulse having pulse width $W_1$ and pulse amplitude $V_{c1}$ exceeds the voltage threshold, $V_{u1}$, for an undesirable activation. If the pulse width is increased to $W_2$, the voltage required for capture, $V_{c2}$, is less than the voltage required for undesirable activation, $V_{u2}$. Therefore, pacing pulses can be delivered at the pacing energy associated with $W_2$, $V_{c2}$ to provide capture of the heart without causing the undesirable activation. The shaded area 150 between the plots 110, 120 indicates the energy parameter values that may be used to produce capture and avoid undesirable activation.

Figure 2:
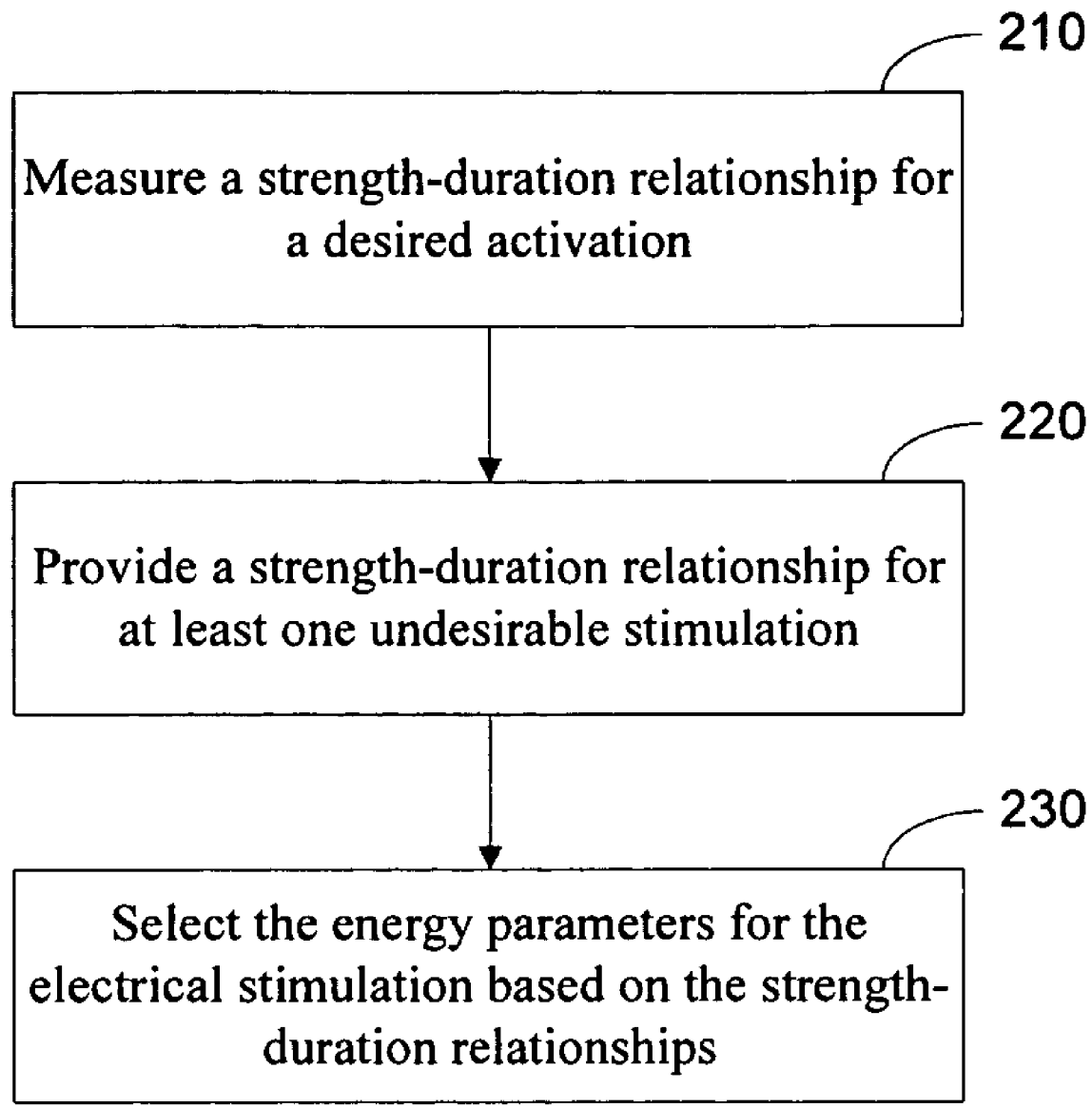
FIG. 2 is a flow chart illustrating a method for determining the energy parameters for therapeutic electrical stimulation in accordance with embodiments of the invention.

Embodiments of the invention are directed to methods and systems for determining one or more energy parameters for therapeutic electrical stimulation, e.g., pulse width and/or pulse amplitude, for electrical stimulation delivered to a patient. FIG. 2 provides a flow chart that illustrates one method for determining the energy parameters. A strength-duration relationship for a desired activation is measured 210. A strength-duration relationship for at least one undesirable activation is provided 220. Although examples are described herein in the context of determining energy parameters that avoid one undesirable activation, extending the approaches to determine energy parameters that avoid multiple undesirable activations will be readily understandable to one skilled in the art.

The strength-duration relationship for the desired activation and/or the strength-duration relationship for undesirable activation may be provided or measured as a single threshold coordinate (W, V). Alternatively, one or more of the strength-duration relationships may be provided or measured as multiple points of the strength-duration plots. The energy parameters, e.g., pulse width and/or pulse amplitude, that produce the desired activation, e.g., capture of the heart, and avoid undesirable activation are selected 230 based on a comparison of the strength-duration relationship for the desired activation and the strength-duration relationship for undesirable activation.

In some implementations, the strength-duration relationship for capture may be determined by a CRM device. For example, testing to determine one or more points of the strength-duration relationship may be automatically performed by a CRM device periodically, upon detection of loss of capture, or triggered by receipt of a command to perform the test. The testing may determine a single point, (W, V), of the strength-duration relationship for capture or may comprise multiple points $(W_i, V_i) = \{(W_1, V_1), (W_2, V_2), \ldots\}$. The strength-duration relationships for one or more types of undesirable activation may be provided or determined as single points of their respective strength-duration plots or may be provided or determined as multiple points.

In various implementations, the strength-duration relationship for the undesirable activation may be determined by theoretical analysis, such as wave dynamics and/or cell modeling, may be determined via population data, and/or may be determined by empirical assessment specific to the patient.

Measurement of the patient-specific strength-duration relationship for undesirable stimulation may be accomplished using sensors capable of detecting the occurrence of the undesirable activation following delivery of a pacing pulse. For example, in some implementations, the undesirable activation comprises cardiac capture from the site of the anodal pacing electrode. This type of undesirable activation is referred to herein as anodal activation. Anodal activation is recognizable by a physician from an electrogram (EGM) or electrocardiogram (ECG) that has been previously collected and stored or displayed in real time. One or more points of the anodal activation strength-duration relationship may be determined by the physician from the EGM or ECG and used for selecting appropriate energy parameters for pacing. For example, the physician may determine whether or not certain test energy parameters caused anodal activation by examining the EGM or ECG. This information may then be input to a device for use as the strength-duration relationship of the undesirable activation.

If multiple-point strength duration plots are known for both capture and the undesirable activation, the energy parameters may be determined based on these two plots. For example, returning to FIG. 1B, the area 150 to the right of the intersection 151 of the strength-duration plots 110, 120 defines the set of energy parameter values that produce capture while avoiding the undesirable stimulation. Energy parameter values that fall within this region 150, or within a modified region 160 that includes appropriate safety margins for pacing 161 and undesirable activation 162, may be selected. In one implementation of the process, the energy parameter values may be automatically selected by the CRM device.

In another implementation of the process, information related to the strength-duration relationships measured for capture and for undesirable activation may be transmitted from the CRM device to a patient-external device, such as a device programmer, advanced patient management system, or other external device. The strength-duration curves may be displayed on a display device for viewing by a physician, such as in an overlaid graph similar to FIG. 1B. Based on the displayed information, the physician may select a voltage threshold value for undesirable activation. For example, the physician may select a voltage threshold value, $V_{uT}$, shown in FIG. 1B. The undesirable activation threshold voltage, $V_{uT}$, may be used to constrain the pacing voltage to a value that will avoid undesirable activation.

Figure 3:
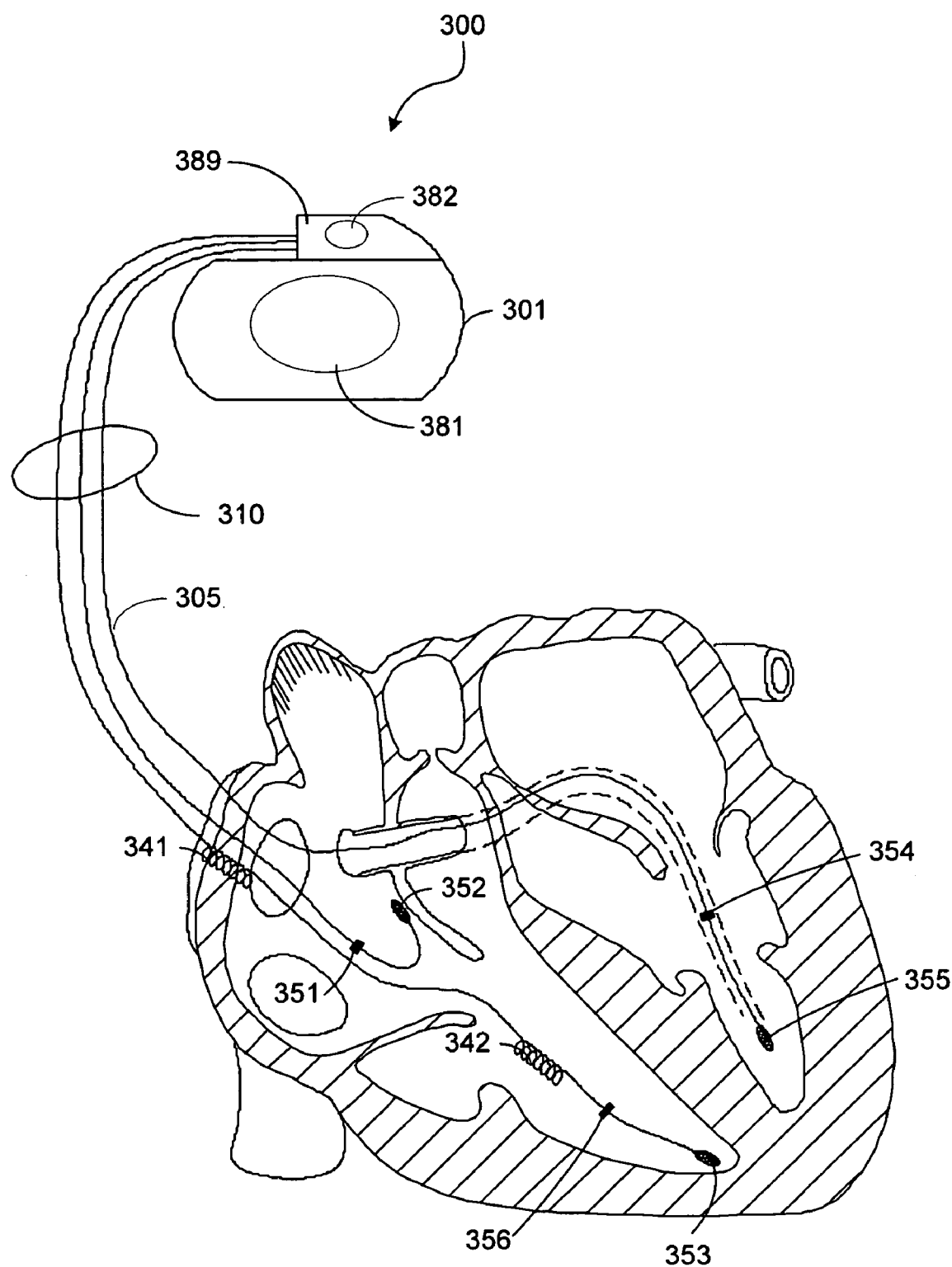
FIG. 3 illustrates a therapy device that includes circuitry capable of measuring energy parameters that produce a desired activation while avoiding undesirable activation in accordance with embodiments of the invention.

The therapy device 300 illustrated in FIG. 3 employs circuitry capable of implementing the techniques described herein for determining energy parameters that produce capture while avoiding undesirable activation. The therapy device 300 includes cardiac rhythm management (CRM) circuitry enclosed within an implantable housing 301. The CRM circuitry is electrically coupled to an intracardiac lead system 310.

Portions of the intracardiac lead system 310 are inserted into the patient's heart. The lead system 310 includes cardiac pace/sense electrodes 351-356 positioned in, on, or about one or more heart chambers for sensing electrical signals from the patient's heart and/or delivering pacing pulses to the heart. The intracardiac sense/pace electrodes 351-356, such as those illustrated in FIG. 3, may be used to sense and/or pace one or more chambers of the heart, including the left ventricle, the right ventricle, the left atrium and/or the right atrium. A therapy control processor controls the delivery of pacing pulses delivered via the electrodes 351-356.

Bipolar electrical stimulation pulses may be delivered via two of the electrodes 351-356. For example, bipolar pacing of the right ventricle may be delivered via electrodes 353 and 356 with the distal tip electrode 353 as the cathode and the proximal ring electrode as the anode. Bipolar pacing of the left ventricle may be delivered via distal and proximal electrodes 355, 354. Bipolar pacing of the right atrium via may be delivered via distal tip 352 and proximal ring 351 electrodes.

Unipolar pacing may be delivered to a heart chamber, for example, using the can 381 and/or indifferent electrode 382 in conjunction with an electrode positioned within or on the paced heart chamber, such as the right ventricular distal tip electrode 353 for right ventricular pacing, the left ventricular distal electrode 355 for left ventricular pacing, or the right atrial distal tip electrode 352 for right atrial pacing. The electrical stimulation pulses delivered to the heart chamber may be used to ensure that the heart beats at a hemodynamically sufficient rate, may be used to improve the synchrony of the heart beats, may be used to increase the strength of the heart beats, and/or may be used for other therapeutic purposes.

The lead system 310 includes defibrillation electrodes 341, 342 for delivering defibrillation/cardioversion shocks to the heart. Electrode/lead configurations other than those illustrated in FIG. 3 may alternatively or additionally used. For example, the electrodes of the CRM device may include epicardial electrodes, subcutaneous electrodes, and or other electrode types.

The left ventricular lead 305 incorporates electrodes 354 and 355 positioned at various locations within the coronary venous system proximate the left ventricle. Stimulating the ventricle at multiple locations in the left ventricle or at a single selected location may provide for increased cardiac output in a patients suffering from congestive heart failure (CHF), for example, and/or may provide for other benefits. Biventricular stimulation pulses may be delivered via electrodes in the left, right or both ventricles according to a phased timing sequence and output configuration that enhances cardiac function.

Portions of the housing 301 of the implantable device 300 may optionally serve as one or multiple can or indifferent electrodes 381, 382. The housing 301 is illustrated as incorporating a header 389 that may be configured to facilitate removable attachment between one or more leads and the housing 301. The housing 301 of the therapy device 300 may include one or more can electrodes 381. The header 389 of the therapy device 300 may include one or more indifferent electrodes 382. The indifferent and/or can electrodes may be used to deliver unipolar pacing or defibrillation/cardioversion.

Communications circuitry is disposed within the housing 301 for facilitating communication between the CRM circuitry and a patient-external device, such as an external programmer or advanced patient management (APM) system. The therapy device 300 may also include sensors and appropriate circuitry for sensing a patient's metabolic need and adjusting the pacing pulses delivered to the heart to accommodate the patient's metabolic need.

In certain embodiments, the therapy device 300 may include circuitry for detecting and treating cardiac tachyarrhythmia via defibrillation therapy and/or anti-tachyarrhythmia pacing (ATP). Configurations providing defibrillation capability may make use of defibrillation coils 341, 342 for delivering high energy shocks to the heart to terminate or mitigate tachyarrhythmia.

Figure 4:
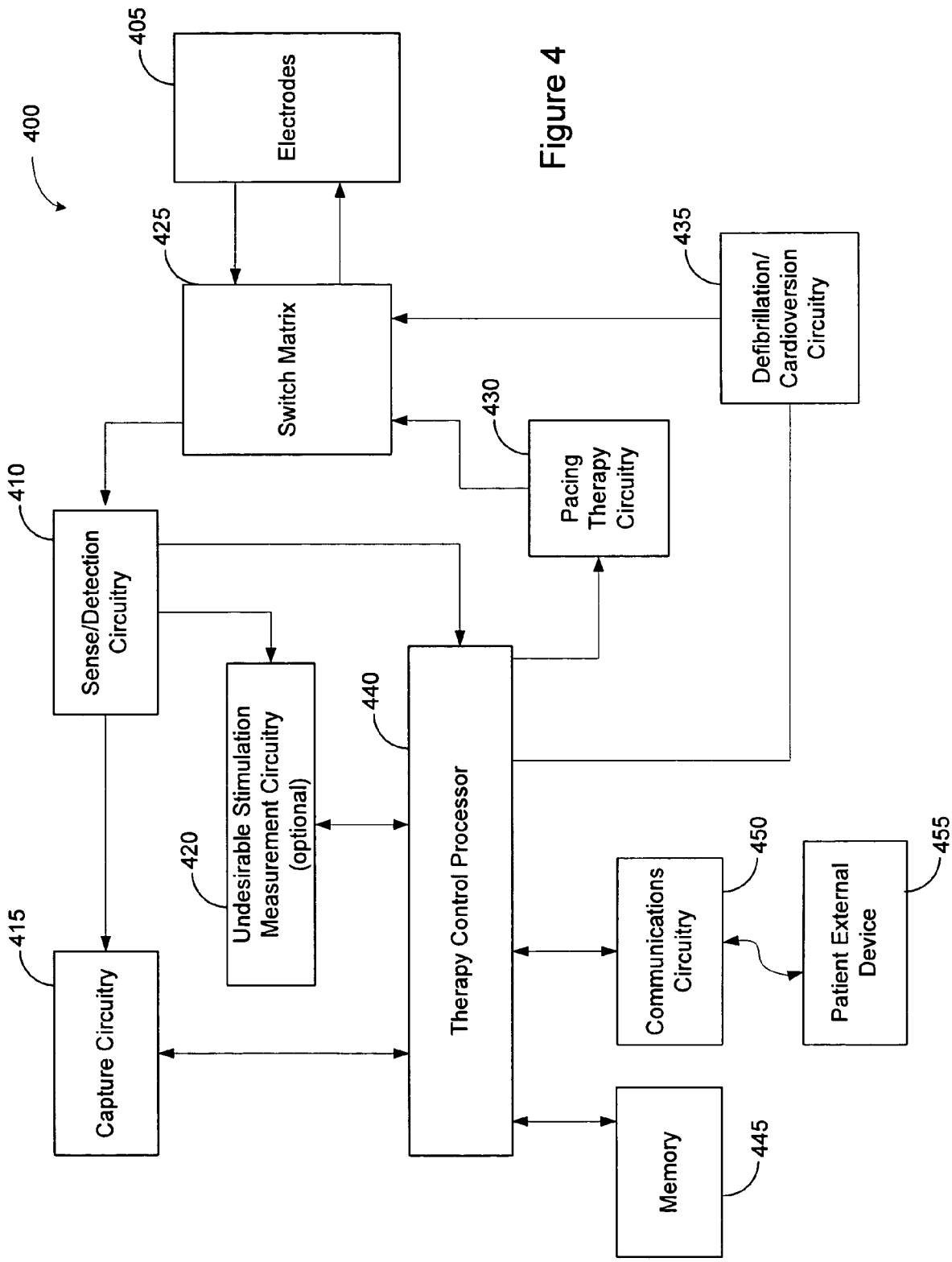
FIG. 4 is a block diagram of a device for determining energy parameters for therapeutic electrical stimulation in accordance with embodiments of the invention.

FIG. 4 is a block diagram of a CRM device 400 that incorporates circuitry for determining energy parameters in accordance with embodiments of the invention. The CRM device 400 includes pacing therapy circuitry 430 capable of detecting arrhythmias and controlling the delivery pacing pulses and/or other forms of electrical stimulation to treat the arrhythmias. The CRM device 400 includes pacing circuitry for treating bradyarrhythmia and may optionally include defibrillation/cardioversion circuitry 435 configured to deliver high energy defibrillation or cardioversion stimulation to the heart for terminating dangerous tachyarrhythmias.

The pacing and/or defibrillation pulses are delivered via multiple cardiac electrodes 405 electrically coupled to a heart disposed at multiple locations within, on, or about the heart. One or more electrodes may be disposed within each heart chamber. The electrodes 405 are coupled to switch matrix 425 circuitry used to selectively couple electrodes 405 to capture measurement circuitry 415, optional undesirable activation measurement circuitry 420, and/or other components of the CRM device 400, via sense/detection circuitry 410 as shown. The capture measurement circuitry 415 may be configured to measure the capture strength-duration relationship or capture threshold (W, V), for example, by periodically initiating step-up, step-down, binary search, or other types of capture threshold tests. The capture measurement circuitry 415, in conjunction with other components of the CRM device 400, may be configured to perform measurements to determine single-point capture thresholds and/or may be configured to determine and store a multiple-point strength-duration relationships for capture of one or more heart chambers.

Optionally, in one configuration, the CRM device 400 includes undesirable activation measurement circuitry 420. The undesirable activation measurement circuitry 420, if used, may be configured to measure one or more points of the strength-duration relationships for one or more undesirable activations.

In another configuration, one or more points of a strength-duration curve for an undesirable activation may be transmitted to the CRM device 400 via a patient-external device 455, such as a programmer, advanced patient management server, or other device, via communications circuitry 450.

The strength-duration relationship values, whether measured from the patient, or received via the external device, are used by the therapy control processor 440 to select energy parameters for pacing that provide for capture of the heart while avoiding undesirable stimulation. The therapy control processor may perform capture tests, for example, periodically, if loss of capture is detected, or on command, to determine the pacing energy parameters that produce capture and avoid undesirable activation. If the testing fails to identify pacing energy parameters that produce capture and avoid undesirable activation, the therapy control processor 440 may generate an alert that can be communicated to the external device 455 via the communication circuitry 450.

In addition to using the strength-duration relationships for setting pacing energy parameter values, the values obtained during repeated strength-duration measurements may be stored in memory 445 along with the selected pacing energy parameters. The stored strength-duration relationships and/or pacing energy parameters may be downloaded to an external device 455 periodically or on command via the communications circuitry 450. The strength-duration plots and/or selected energy parameters can be displayed on the external device or may be used to generate a report accessible to a physician, certified professional, and/or advanced patient management system. The information may be used to track changes over time in the strength-duration plots and/or selected energy parameters.

Figure 5:
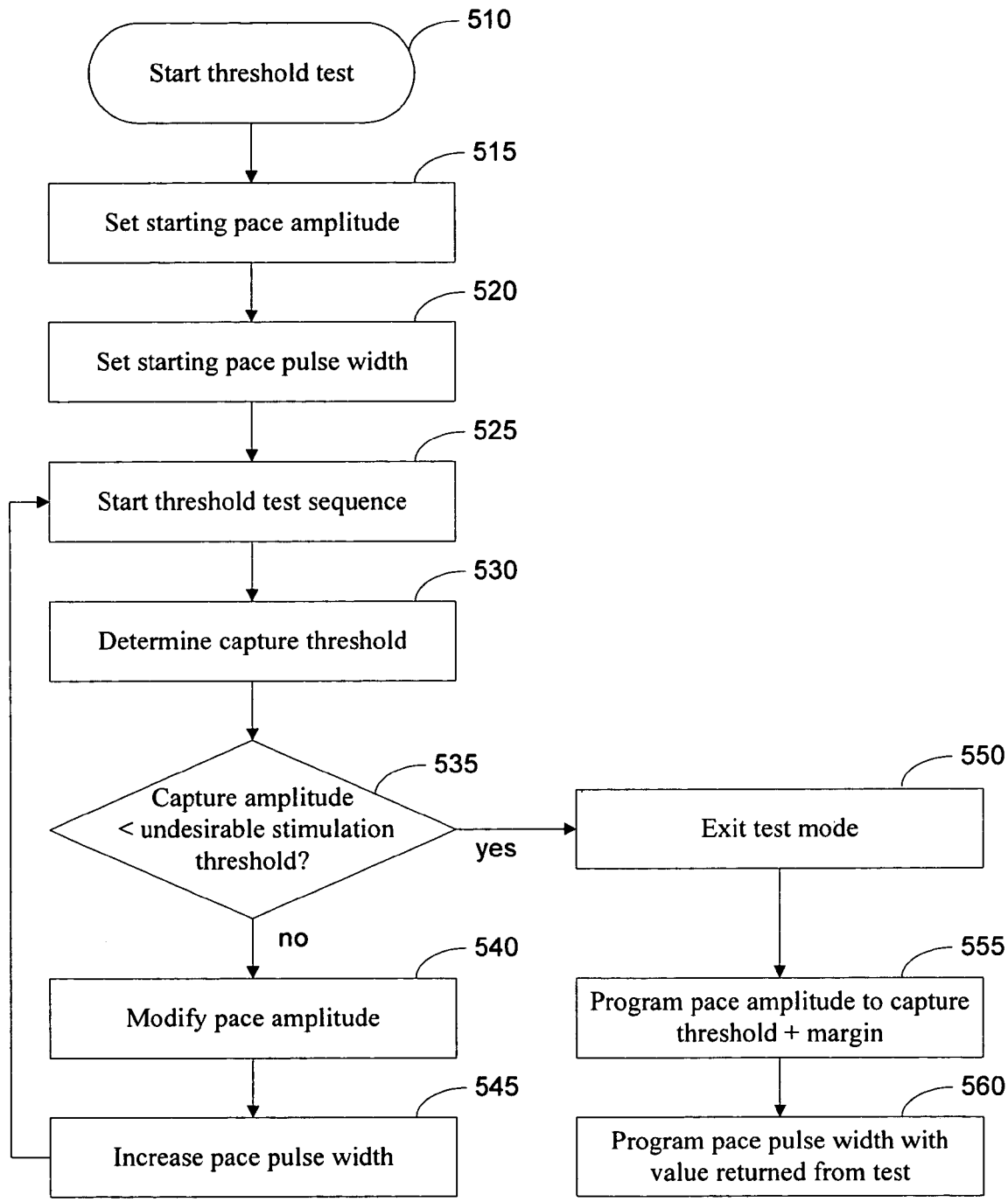
FIGS. 5 and 6 are flow charts illustrating methods for determining cardiac pacing energy parameters in accordance with embodiments of the invention.

FIG. 5 is a flow chart of a method for determining pacing energy parameters in accordance with one embodiment. In this implementation, prior to the start 510 of a test to determine the pacing amplitude and pulse width, a undesirable activation pulse amplitude threshold has been determined by the device, or otherwise provided. The undesirable activation threshold may be a fixed value across all patients, may be provided for the particular patient from population data or theoretical analysis, or may be determined from measurements made by the CRM device as previously discussed.

The amplitude for the pacing pulse is set 515 to a beginning pace amplitude, such as the amplitude value previously used for pacing plus a margin, where the margin may be a fixed or programmable value. For example, beginning pace amplitude may ensure that the pacing energy exceeds the capture threshold and/or exceeds the undesirable activation threshold. The pulse width for the pacing pulse may also be set 520 to a predetermined value, such as the previous pulse width threshold value. A capture threshold test sequence is performed 525, which may involve a step-up, step-down, binary search, or other type capture threshold measurement for determining 530 the pulse amplitude threshold for capture.

If the pulse amplitude for capture determined by the capture threshold test is greater than 535 the threshold value for the undesirable activation, the pulse amplitude and/or width may be modified and the test repeated. The decision that modifies the pacing energy parameters may involve various methods for determining how to set the pacing energy parameters. In various implementations, the pulse amplitude and/or pulse width may be modified during the capture threshold test based on the strength-duration relationship for undesirable activation and/or a strength-duration relationship for capture. The determination and use of patient-specific strength-duration relationships promotes selection of optimal, patient-specific pacing energy parameters while improving testing efficiency and minimizing testing to determine pacing energy parameters.

In one particular implementation, the pulse amplitude is set 540 to the test starting value, or to another predetermined value, such as the undesirable stimulation amplitude threshold value. The pulse width is increased 545 and the test is repeated 525. The process 525-545 is repeated until the pulse amplitude for capture is less than 535 the pulse amplitude threshold for the undesirable stimulation.

If the pulse amplitude for capture is less than 535 the pulse amplitude threshold for the undesirable stimulation, the test mode is exited, see block 550. The pacing pulse amplitude is programmed 555 to the capture threshold value returned by the capture threshold test plus a safety margin. The pacing pulse width is programmed 560 to the value returned by the capture threshold test.

Figure 6:
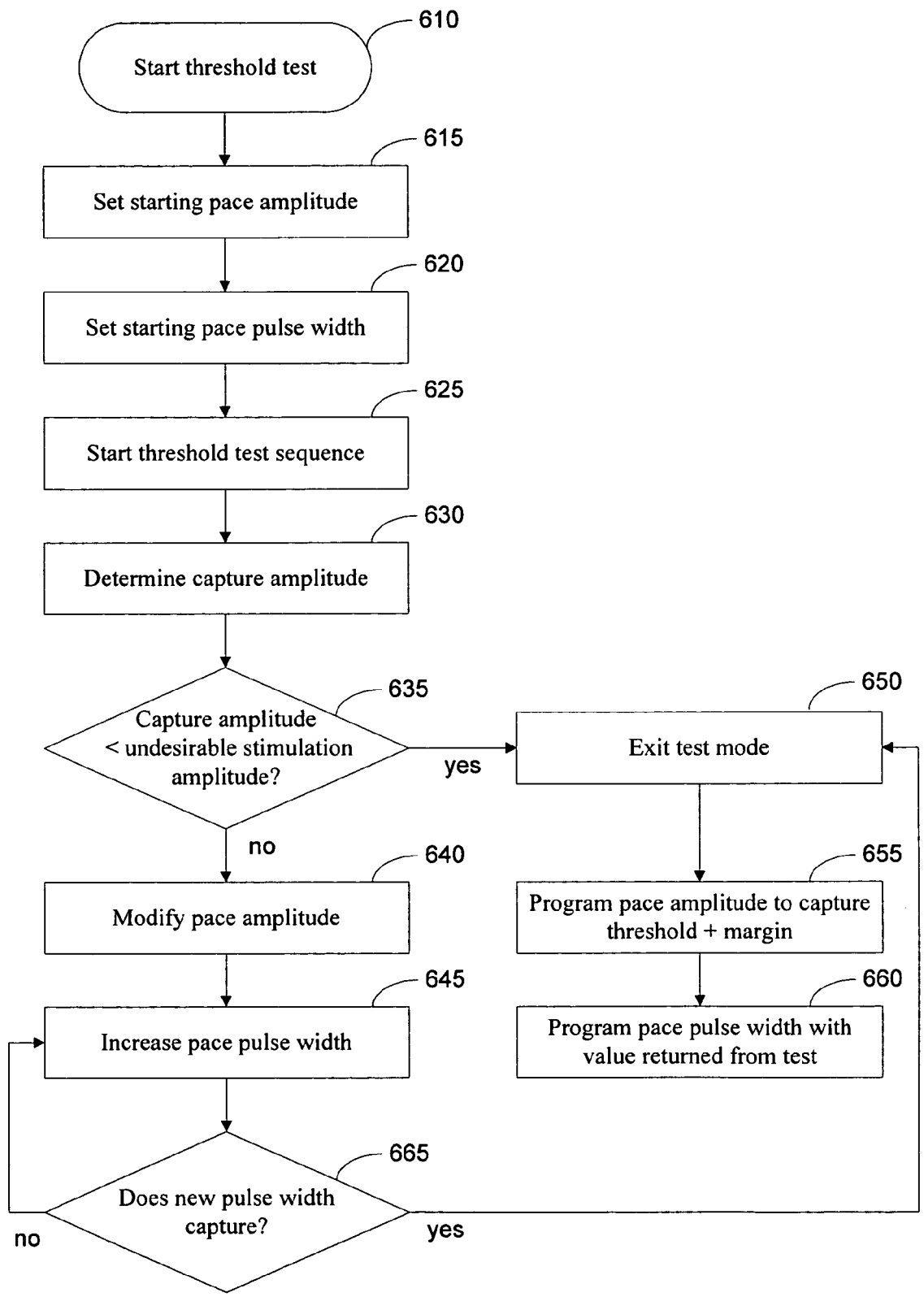

FIG. 6 is a flow chart of another method for performing a capture test to determine pacing energy parameters in accordance with one embodiment. As before, in this implementation, prior to the start 610 of the test, a undesirable activation pulse amplitude threshold has been determined by the device, or otherwise provided. The amplitude for the pacing pulse is set 615 to a beginning pace amplitude, such as the previous threshold amplitude value plus a fixed or programmable margin as previously discussed. The pulse width for the pacing pulse may also be set 620 to a predetermined value, such as the previous pulse width threshold value.

The capture threshold test sequence is performed 625, which may involve a step-up, step-down, binary search, or other type capture threshold measurement for determining 630 the pulse amplitude threshold for capture.

If the pulse amplitude for capture determined by the capture threshold test is less than 635 the threshold value for the undesirable activation, the process exits 650 the test mode. If the pulse amplitude for capture is greater than 635 the threshold value for the undesirable activation, the pulse amplitude and/or pulse width is modified. In various implementations, the pulse amplitude and/or pulse width may be modified during the capture threshold test based on the strength-duration relationship for undesirable activation and/or a strength-duration relationship for capture. In one particular implementation, the pulse amplitude is set 640 to the undesirable stimulation threshold value minus a safety margin. The pulse width is incrementally increased 645 until capture is detected 665.

When capture is detected 665, the test mode is exited 650. The pacing pulse amplitude is programmed 655 to the value returned by the capture threshold test plus a safety margin. The pacing pulse width is programmed 660 to the value returned by the capture threshold test.

The embodiments of the invention described herein may be used in conjunction with any type of therapeutic device in which stimulation thresholds are used to provide for appropriate energy parameter settings, including cardiac and neurological stimulation devices. The flexibility and automaticity of the approach allow for use in implanted devices where manual and/or automatic energy parameter selection may be implemented. Use of the methods and systems described herein may be used to provide for enhanced patient safety and comfort as well as therapy effectiveness. Use of patient-specific strength-duration relationships allows safety, efficacy and optimization of therapy individually for each patient. The approaches described herein may be used along with remote follow-up or patient management systems for providing additional data that may be used to inform physician decisions regarding the titration of therapy.

The components, functionality, and structural configurations depicted herein are intended to provide an understanding of various features and combination of features that may be incorporated in an implantable pacemaker/defibrillator. It is understood that a wide variety of cardiac monitoring and/or stimulation device configurations are contemplated, ranging from relatively sophisticated to relatively simple designs. As such, particular cardiac device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A therapy device, comprising:
   electrodes configured to deliver therapeutic electrical stimulation;
   measurement circuitry configured to measure a capture threshold during a capture threshold test, to modify at least one capture threshold test energy parameter based on a strength-duration relationship for at least one undesirable nerve or muscle activation, to perform an additional capture threshold test to determine an additional capture threshold using the modified test energy parameter, and to determine energy parameters for the therapeutic electrical stimulation that produce capture and avoid the undesirable nerve or muscle activation using the additional capture threshold; and a therapy control processor configured to use the energy parameters for delivery of the therapeutic electrical stimulation;

wherein the modified test energy parameter comprises a pulse amplitude set to an undesirable nerve or muscle activation threshold which is based on the strength-duration relationship for the undesirable nerve or muscle activation.

2. A device of claim 1, wherein:

the electrodes are electrically coupled to a heart;

the therapeutic electrical stimulation comprises pacing pulses to the heart; and the measurement circuitry comprises circuitry configured to measure the strength-duration relationship of the undesirable activation.

3. The device of claim 1, wherein:

the strength-duration relationship for undesirable activation comprises a multiple-point strength-duration curve for undesirable activation.

4. The device of claim 1, wherein the undesirable activation comprises activation of a phrenic nerve.

5. The device of claim 1, wherein the undesirable activation comprises muscle activation.

6. The device of claim 1, wherein the at least one modified test energy parameter comprises a pulse width.

7. The device of claim 1, wherein the at least one modified test energy parameter comprises a pulse amplitude.

8. The device of claim 1, wherein the measurement circuitry is configured to determine a desired activation strength-duration curve based on pulses of delivered therapeutic electrical stimulation that produced the desired activation, and the measurement circuitry is configured to determine the undesirable activation strength-duration curve based on multiple pulses of delivered therapeutic electrical stimulation that produced the undesirable activation.

9. The device of claim 1, wherein the strength-duration relationship for undesirable activation is based on population data.

10. The therapy device of claim 1, wherein the measurement circuitry is configured to perform the additional capture threshold test by increasing a pulse width until capture is detected.

* * * * *